United States Patent
Flashinski et al.

(10) Patent No.: US 6,309,986 B1
(45) Date of Patent: *Oct. 30, 2001

(54) MAT FOR DISPENSING VOLATILE MATERIALS

(75) Inventors: Stanley J. Flashinski, Racine County; Nancy J. Vnuk; Lori J. Bootz, both of Milwaukee County, all of WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/307,150

(22) Filed: May 7, 1999

(51) Int. Cl.$^7$ ........................................................ A61L 9/02
(52) U.S. Cl. ................... 442/125; 428/308.4; 392/386; 392/390; 392/391
(58) Field of Search ................... 428/34.1, 34.2, 428/40.1, 304.4, 905, 907, 308.4; 424/84, 409, 410, 414, 416; 239/34, 54, 55, 60, 56; 43/124, 125, 129, 132.1; 422/37; 392/386, 391, 370, 393; 219/543, 546, 547; 442/125

(56) References Cited

U.S. PATENT DOCUMENTS

| | | | |
|---|---|---|---|
| 2,372,371 | * 3/1945 | Eisner | 21/120 |
| 2,535,802 | * 12/1950 | Libson | 21/120 |
| 2,742,342 | * 4/1956 | Dew et al. | 21/53 |
| 3,655,129 | 4/1972 | Seiner | 239/60 |
| 4,160,335 | * 7/1979 | Von Kohorn et al. | 43/131 |
| 4,214,146 | * 7/1980 | Schimanski | 218/274 |
| 4,639,393 | * 1/1987 | Von Kohorn et al. | 428/304.4 |
| 4,647,433 | * 3/1987 | Spector | 422/125 |
| 4,666,767 | * 5/1987 | Von Kohorn et al. | 428/304.4 |
| 4,927,635 | 5/1990 | Loschiavo | 424/409 |
| 4,990,381 | 2/1991 | Holzner | 428/35.3 |
| 5,071,704 | * 12/1991 | Fischel-Ghodsian | 428/354 |
| 5,252,387 | 10/1993 | Samson et al. | 428/248 |
| 5,532,043 | 7/1996 | Terashi et al. | 428/152 |
| 5,637,401 | * 6/1997 | Berman et al. | 252/315.2 |
| 6,031,967 | * 2/2000 | Flashinski et al. | 392/390 |
| 6,154,607 | * 11/2000 | Flashinski et al. | 392/390 |

FOREIGN PATENT DOCUMENTS 2166653A   7/1985   (GB) .

OTHER PUBLICATIONS

Patent Abstracts of Japan, Publication No. 63122603.
Database WPI, XP002147906.

\* cited by examiner

*Primary Examiner*—Blaine Copenheaver
*Assistant Examiner*—Alicia Chevalier

(57) ABSTRACT

Disclosed herein are mats for dispensing volatile vapors such as insecticides. The mats are multi-layered. One layer is a carrier layer impregnated with the volatile. It is secured to at least one metal layer. The metal layer spreads the heat from a heater, thereby minimizing hot spots. In other embodiments additional layers are provided to provide a further heat distribution or temperature step down. An air gap can be provided between two of the layers.

7 Claims, 1 Drawing Sheet

MAT FOR DISPENSING VOLATILE MATERIALS

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

This invention relates to dispensing volatile materials such as pest control materials, including but not limited to insecticides and insect repellents, and fragrances. More particularly, it relates to volatile material-containing mats that are employed in conjunction with electrical, gas, flammable liquid, or wax-fueled heaters or other sources of heat. One type of electrical heater used for this purpose is sold by S.C. Johnson & Son, Inc. under the trademark FUYI VAPE™.

It is known in the art to impregnate a solid, porous cellulosic mat with a volatile material or to place a volatile material in a pan-like metal structure. These mats and pans are placed on heaters to cause the volatile material to vaporize into the atmosphere.

A problem with the metal pan-like structures is that for typical heaters they can cause a volatile material to be exposed to too much heat. This can cause the volatile to be used up too fast or be deteriorated or destroyed through thermal degradation.

The mats have similar problems and also have problems with respect to their being exposed to differing temperatures across a heater surface. Low-cost existing heaters often have hotter regions at certain points along their burner surface. The mats therefore can have uneven and inefficient vaporization.

The above problems are of increased concern for extended longevity products intended to be used for a week or more. Merely adding additional volatile to increase product capacity and longevity does not work well because prolonged exposure of volatiles to too high temperatures can degrade or destroy the volatile and because, with hot temperatures, a disproportionate amount of the volatile can be driven off initially, with an insufficient amount surviving to be released in useful amounts at a later time.

Another design consideration is that existing heaters, for safety and other reasons, often only accept slab-like inserts having a small cross-sectional shape, necessary to fit into a small heater loading port or opening. Thus, any solution to the extended longevity problem preferably takes into account size restrictions imposed by existing heaters.

Yet another critical design consideration is cost. Mats of this type are often used in countries that have very modest average annual incomes. To have much practical application in those countries, the mats must be inexpensive.

As such, it can be seen that a need exists for an improved volatile dispensing device.

BRIEF SUMMARY OF THE INVENTION

In one aspect, the invention provides a mat for dispensing volatile vapors when the mat is heated. The mat has a carrier layer having a solid carrier material with a volatile material placed therein, the carrier material being constructed and arranged so as to emit the volatile material when heated. There is also a first metal layer secured to a side of the carrier layer. Preferably the first metal layer is secured adhesively, although crimping, riveting, and other ways to attach two layers can be used and would fall within the spirit and scope of the invention. Unless a contrary result is specified, all layers secured to each other, as described herein, can be secured by any of these or equivalent ways of doing so, although adhesive attachment is generally preferred. When a side of the metal layer opposite the carrier material is heated, the metal layer distributes heat along itself and transmits heat to the carrier.

The volatile material is preferably an insecticide, insect repellent, developmental controller, or other insect control material. Alternatively, the volatile material may be a fragrance, deodorizer, or other air quality modifying material. The carrier material is preferably a cellulosic material.

In a second embodiment, the mat also has a non-metallic layer secured to a side of the first metal layer opposite the carrier layer. The non-metallic layer provides a temperature step down from the temperature of the heater to that experienced by the volatile material. Preferably, there is also a second metal layer secured to a side of the non-metallic layer opposite the first metal layer. This embodiment provides further temperature step down and distribution.

In still another embodiment the last layer most distant from the volatile material is a non-metallic layer, which then contacts the heater. This embodiment is particularly desirable for heaters that have poor temperature control.

In yet another embodiment the mat has a non-metallic layer with leg portions extending therefrom, preferably extending downwardly, away from the volatile material, and the mat also has a second metal layer adhesively secured to the legs opposite the first metal layer. By this arrangement, a cavity is provided between a portion of the non-metallic layer and the second metal layer. This embodiment is particularly desirable with respect to heaters that occasionally provide temperature spikes.

The mats of the present invention spread heat more uniformly across their surface, as well as reduce excess temperatures that may be developed from poorly controlled heaters or heaters designed for use with less temperature sensitive volatiles.

These and still other features and advantages of the present invention will be apparent from the description which follows. The following description is of the preferred embodiments. The claims should be looked to in order to understand the full scope of the invention.

DETAILED DESCRIPTION

Figure 1:
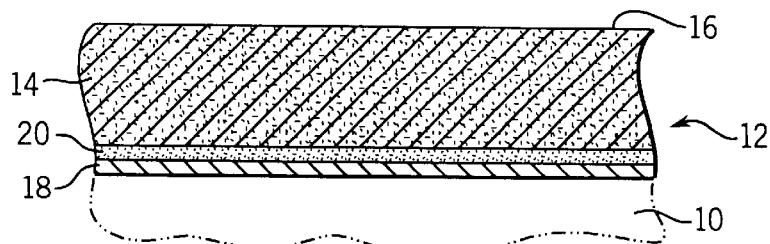
FIG. 1 is a vertical sectional view showing a mat for dispensing volatile materials of the present invention.

FIG. 1 shows in dotted lines a portion 10 of an electrical heater. The heater can be the FUYI VAPE™ heater previously described, except that the single layer mat conventionally used with that heater has now been replaced with a mat of the present invention. The FUYI VAPE™ heater is an electrical-resistance heater having a flat, upwardly exposed plate 10 on/against which is placed a mat generally 12 (or 12A or 12B or 12C) of the present invention. Although the FUYI VAPE™ heater is shown by way of example, other heaters of any type intended for use with comparable mats could be used instead. For purposes of convenient description, the hot heater surface will be designated as being in a "down" direction, with features of mats being referred to as being "upper" or "lower" or "above" or "below" each other. In fact, the hot heater surface of some conventional heaters are vertical, but such variation is not important to an understanding of the mat of the invention.

Mat 12 has an upper, solid carrier layer 14, preferably made of paper or other porous, cellulose-based material. Other solid porous substrates could also be used, such as sintered glass, plastic beads, natural or synthetic fabrics, and other absorbent and adsorbent materials. Carrier layer 14 is impregnated with a volatile 16. When placed over the heater the volatile is released from it when mat 12 is heated.

Under the carrier layer 14 is a first layer 18 of metallic material such as aluminum. It is secured to the carrier layer 14, preferably by an adhesive 20. The preferred adhesive is a polymeric adhesive sold as adhesive "711" available from Manufacturer Resources Inc. of New Berlin, Wis. Other adhesives could also be used, such as high temperature resistant acrylics and urethanes. When selecting adhesives it is desirable that the adhesive be heatstable and be able to bond a metal layer to a non-metallic layer. Further, it is preferred that the insulating characteristics of the adhesive be minimal.

The first metal layer 18 distributes heat across itself and then to carrier layer 14. This helps reduce hot spots and to some extent provides a temperature step down.

FIGS. 2–5 illustrate alternative embodiments, wherein similar components are indicated with similar reference numbers, except with an A, B, or C suffix.

Figure 2:
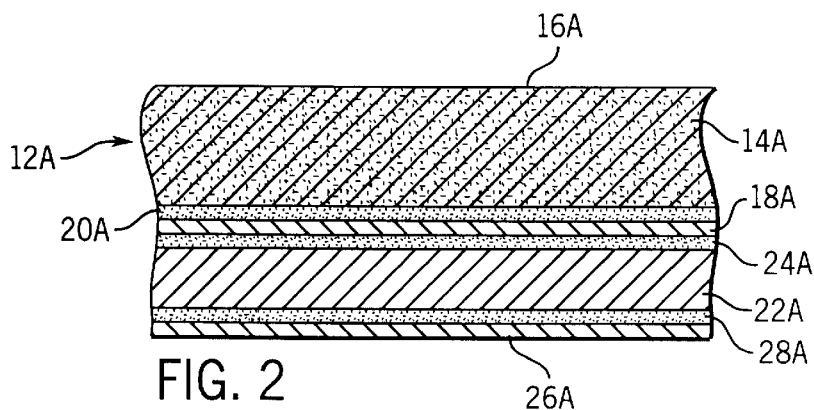
FIGS. 2, 3, and 4 are views similar to FIG. 1, albeit showing three additional embodiments.
Figure 3:
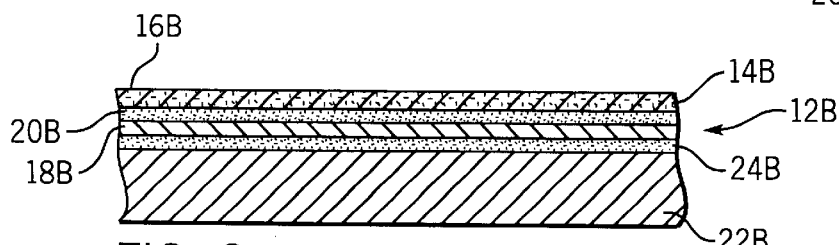
Figure 4:
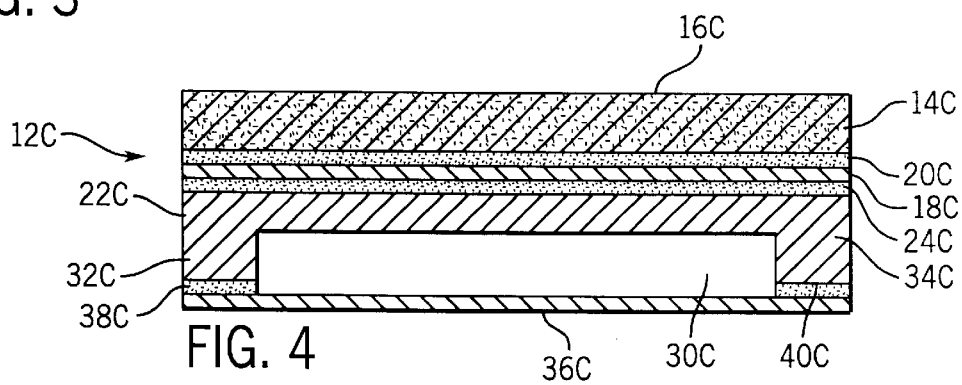
Figure 5:
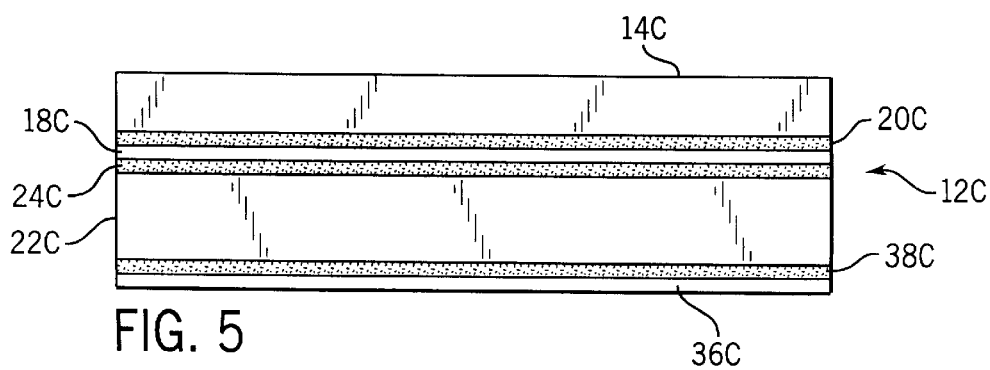
FIG. 5 is both a left side and frontal view of the FIG. 4 embodiment.

Referring to FIG. 2, mat 12A includes a carrier layer 14A impregnated with volatile material 16A as well as first and second metal layers 18A and 26A. It also includes a layer 22A of low heat-conductive material such as fiber mat, ceramic, cellulose, etc. If desired and correctly chosen, the same material used for carrier layer 14A also can be used for layer 22A, albeit without the volatile. Preferably, adhesives 20A, 24A and 28A, which can all be the "711" adhesive or similar adhesives, secure the layers together. Embodiment 12A offers additional uniform heat distribution as well as an even more pronounced temperature step down.

Embodiment 12B (shown in FIG. 3) is similar to embodiment 12A, except that it does not have the metallic layer 26A or intervening adhesive 28A. Non-metallic material 22B is placed in direct contact with the heater.

Embodiment 12C (shown in FIGS. 4 and 5) is somewhat similar to embodiment 12B, except that the low heat-conductive, non-metallic layer 22C has a cavity portion 30C provided by legs 32C and 34C. This cavity provides an air gap permitting even further reduction of hot spots near the center of the mat. Second metal layer 36C extends from one leg 32C to the other 34C, the metal layer being secured to the legs 32C and 34C by adhesive 38C and 40C. The cavity can be open to the air at the sides, or, as shown in the drawings, can be completely enclosed at the sides.

The volatile material is preferably one of (or mixtures of) known insecticides and insect repellents. Particularly preferred are organic phosphorous insecticides, lipidamide insecticides, natural repellents as citronella oil, natural pyrethrins and pyrethrum extract, and synthetic pyrethroids. Suitable synthetic pyrethroids are allethrin as D-allethrin, Pynamin®, benfluthrin, bifenthrin, bioallethrin as Pynamin Forte®, S-bioallethrin, esbiothrin, esbiol, bioresmethrin, cycloprothrin, cyfluthrin, beta-cyfluthrin, cyhalothrin, lambda-cyhalothrin, cypermethrin, alpha-cypermethrin, beta-cypermethrin, cyphenothrin, deltamethrin, empenthrin, esfenvalerate, fenpropathrin, fenvalerate, flucythrinate, tau-fluvalinate, kadethrin, permethrin, phenothrin, prallethrin as Etoc®, resmethrin, tefluthrin, tetramethrin or tralomethrin. Other volatile insecticides as described in U.S. Pat. No. 4,439,415 can also be employed. The disclosure of that patent is incorporated herein in full, by reference, as are the disclosures of all patents or publications referred to herein.

Most preferred is Pynamin Forte®. Particularly desirable performance has been achieved by dissolving 40 mg of this active ingredient in 60 mg of the hydrocarbon solvent Isopar M (from Exxon). 100 mg of the resulting solution is used to impregnate the cellulose portion of a substantially flat mat having 22 mm×35 mm top view dimension. Preferably the cellulose layer is approximately 2.5 mm thick and is adhered to a 0.5 mm thick aluminum foil using 10 mg of the 711 adhesive prior to impregnation.

Deodorizers may also be used with the mat of the invention, such as a terpene based deodorizer fragrance. Further, volatile fragrances, disinfectants, or other air quality modifying agents may be used, such as glycols, trimethylene, and dipropylene. In addition, organic acids that are compatible with the use of the substrate and the atmosphere can also be utilized.

The invention is not to be limited to the specific embodiments shown. Rather, the claims should be looked to in order to appreciate the full scope of the claimed invention.

INDUSTRIAL APPLICABILITY

The invention provides mats for dispensing volatile materials such as insecticides. The mats are particularly useful in controlling mosquitoes over extended periods.

What is claimed is:

1. A volatile dispensing system, comprising a heater and a mat, the mat comprising:
   a. a solid carrier layer having a volatile material impregnated therein, the carrier layer being constructed and arranged so as to emit the volatile material when heated by the heater; and
   b. a first exposed metal layer secured to a side of the carrier layer facing the heater, whereby, upon heating of a side of the metal layer opposite the carrier layer, the metal layer will distribute heat along itself and transmit heat to the carrier layer;

wherein the carrier layer is entirely uncovered on the side opposite the side that is secured to the metal layer.

2. The system of claim 1, wherein the volatile material is selected from the group consisting of insecticides, insect repellents, insect developmental controllers, and combinations thereof.

3. The system of claim 1, wherein the carrier layer is a cellulosic material.

4. A volatile dispensing system, comprising a heater and a mat, the mat comprising:
   a. a solid carrier layer having a volatile material impregnated therein, the carrier layer being constructed and arranged so as to emit the volatile material when heated by the heater;
   b. a first exposed metal layer secured to a side of the carrier layer facing the heater, whereby, upon heating of a side of the metal layer opposite the carrier layer, the metal layer will distribute heat along itself and transmit heat to the carrier layer;

c. a non-metallic layer secured to a side of the first exposed metal layer; and d. a second metal layer secured to a side of the non-metallic layer opposite the first exposed metal layer.

5. The system of claim 4, wherein the non-metallic layer has leg portions extending therefrom.

6. The system of claim 5, wherein a cavity is provided between a portion of the non-metallic layer and the exposed metal layer.

7. A volatile dispensing system, a heater; and a mat emitting volatile vapors when heated by the heater, the mat comprising:

i. a solid carrier layer having a volatile material impregnated therein;

ii. a first metal layer secured to a side of the carrier layer; and iii. a non-metallic layer secured to a side of the first metal layer opposite the carrier layer and facing the heater;

whereby the metal layer distributes heat from the heater to the carrier layer, and wherein the carrier layer is entirely uncovered on the side opposite the side that is secured to the metal layer.

* * * * *

UNITED STATES PATENT AND TRADEMARK OFFICE
CERTIFICATE OF CORRECTION

PATENT NO.    : 6,309,986 B1
DATED         : October 30, 2001
INVENTOR(S)   : Stanley J. Flashinski, Nancy J. Vnuk and Lori J. Bootz It is certified that error appears in the above-identified patent and that said Letters Patent is hereby corrected as shown below:

<u>Column 5,</u>
Line 10, after "system," insert -- comprising: --.

Signed and Sealed this

Fourteenth Day of May, 2002

*Attest:*

JAMES E. ROGAN
*Attesting Officer*    *Director of the United States Patent and Trademark Office*